(12) United States Patent
Yamada et al.

(10) Patent No.: US 6,534,553 B1
(45) Date of Patent: Mar. 18, 2003

(54) HYDROGENATION OF CARBON MONOXIDE USING SULFIDE CATALYSTS

(75) Inventors: Muneyoshi Yamada, Sendai (JP); Naoto Koizumi, Sendai (JP)

(73) Assignee: President of Tohoku University, Sendai (JP)

( * ) Notice: Subject to any disclaimer, the term of this patent is extended or adjusted under 35 U.S.C. 154(b) by 0 days.

(21) Appl. No.: 09/986,905

(22) Filed: Nov. 13, 2001

(30) Foreign Application Priority Data

Jul. 17, 2001 (JP) ........................................ 2001-217017

(51) Int. Cl.$^7$ ............................................... C07C 27/00
(52) U.S. Cl. ...................... 518/715; 518/700; 518/717
(58) Field of Search ................ 518/700, 715, 518/717

(56) References Cited

U.S. PATENT DOCUMENTS

| | | |
|---|---|---|
| 4,119,656 A | 10/1978 | Poutsma et al. |
| 4,199,522 A * | 4/1980 | Murchison et al. ......... 518/714 |
| 4,289,709 A | 9/1981 | Kaiser |
| 4,289,710 A | 9/1981 | Kaiser |
| 4,749,724 A | 6/1988 | Quarderer et al. |

FOREIGN PATENT DOCUMENTS

| | | |
|---|---|---|
| JP | 55-139324 | 10/1980 |
| JP | 55-139325 | 10/1980 |

OTHER PUBLICATIONS

H. E. Curry–Hyde, "Natural Gas Conversion II", Studies in Surface Science and Catalysis 81, Elsevier, 1994, pp. 43–71.
A. Gotti, et al., "Basic Metal Oxides as Co–Catalysts Conversion of Synthesis Gas to Methanol on Supported Palladium Catalysts", Journal of Catalysis 175, 302–311, 1998, pp. 302–311.

* cited by examiner

*Primary Examiner*—J. Parsa
(74) *Attorney, Agent, or Firm*—Oblon, Spivak, McClelland, Maier & Neustadt, P.C.

(57) ABSTRACT

A method of producing synthetic fuels by hydrogenating carbon monoxide comprising contacting a feed gas containing carbon monoxide and hydrogen with a catalyst comprising:

(1) a supported metal sulfide comprising Pd and at least one promoter selected from the group consisting of alkali metal, alkaline earth metal, and rare earth elements, and optionally (2) solid acid.

22 Claims, No Drawings

HYDROGENATION OF CARBON MONOXIDE USING SULFIDE CATALYSTS

CROSS-REFERENCE TO RELATED APPLICATIONS

This application is based upon and claims the benefit of priority from the prior Japanese Patent Application No. 2001-217017, filed Jul. 17, 2001, the entire contents of which are incorporated by reference.

BACKGROUND OF THE INVENTION

1. Field of the Invention

This invention relates to a process for hydrogenating carbon monoxide. More specifically, this invention relates to a process for producing synthetic fuels of low environmental impact from synthesis gas. In one aspect, this invention concerns a catalyst for use in the hydrogenation of carbon monoxide.

2. Description of the Related Art

Various useful organic chemicals have been produced from carbon resources like petroleum, coal, natural gas, and biomass in the following manner. Firstly, a synthesis gas, a mixture of carbon monoxide and hydrogen, is produced through a reforming reaction or a coal gasification. The synthesis gas is then allowed to react on specific catalysts at high temperature and at high pressure, thus converted to hydrocarbons or oxygenates.

These organic chemicals thus obtained will suppress the emission of toxic substances when used as fuel, since they contain little sulfur and nitrogen compounds owing to their distinctive manufacturing processes. In particular, methanol, which is mostly produced from synthesis gases and used as an alternative fuel or a gasoline additive, has recently received much attention as a hydrogen source for the fuel cell. In the stream of rising environmental-conscious, an improved manufacturing method with higher productivity is desired.

In the reaction of synthesis gases, catalysts including metals such as Cu, Fe, and Co are generally used. Typical review articles are in the text "Studies in surface science and catalysis, vol. 81, NATURAL GAS CONVERSION", H. E. Curry-Hyde, R. F. Howe, Elsevier (1994).

While Cu is widely used for the production of methanol, it is also known in the art that Rh, Pd, Ir and Pt have considerable activity for the alcohol synthesis and that the activity may be promoted by the addition of alkali metal, alkali earth metal, and rare earth elements.

For instance, U.S. Pat. No. 4,119,656 discloses that methanol is selectively produced on a silica supported Pd (Pd/$SiO_2$) catalyst. U.S. Pat. Nos. 4,289,709 and 4,289,710 disclose the promoting effect of Li, Mg, Sr, Ba, Mo, and Ca in the methanol synthesis on a Pd/$SiO_2$ catalyst. A. Gotti and R. Prins in Journal of Catalysis, 175, 302–311(1998) have mentioned the promoting effect of Ca and La on activity and selectivity in the methanol synthesis.

Among these catalysts, Cu catalysts are commercially used for the methanol synthesis because of their low cost and availability, in spite of the drawbacks of requiring high temperature and high pressure conditions. However, Cu catalysts are easily poisoned by various chemical substances in feed gases, particularly by a trace amount of sulfur compounds such as hydrogen sulfide. To avoid this sulfur poisoning, sulfur compounds must be reduced far less than 1 ppb through a desulfurization facility before the reforming or hydrogenation reaction process. Consequently, the use of Cu catalysts make the manufacturing process complicated and expensive.

Nevertheless, misoperation or accidents leading to contamination of sulfur compounds might damage the catalysts.

On this sulfur poisoning, Jpn. Pat. Appln. KOKAI Publication Nos. 55-139324 and 55-139325 disclose a production process of hydrocarbons with sulfur tolerant catalysts that consist essentially of the metal, oxide or sulfide of Mo, W, Re, Ru, Ni, Pd, Rh, Os, Ir or P, and alkali metal or alkaline earth metal. In these applications, it is noted that a catalyst consisting of $MoO_3$, $K_2O$ and carborundum shows no remarkable change in activity and gaseous alkene selectivity even when a synthesis gas contains 20 ppm of hydrogen sulfide.

U.S. Pat. No. 4,749,724 discloses that C1–C4 alcohols are produced from a synthesis gas containing hydrogen sulfide at high pressures around 10 MPa on a sulfided Mo, W or Re catalyst added with alkali metal or alkaline earth metal.

As mentioned above, Cu catalysts are deactivated by sulfur compounds, so that the content of sulfur compounds must be lowered far less than 1 ppb by means of upstream desulfurization units. On the other hand, aforementioned sulfide catalysts containing Mo, W or Re require high pressure conditions to achieve proper activity and selectivity.

BRIEF SUMMARY OF THE INVENTION

The object of the present invention is to provide a method for hydrogenating carbon monoxide with high productivity under mild conditions and with a simple manufacturing process. It is another object of the present invention to provide sulfide catalysts with high durability, especially excellent sulfur tolerance in the production of synthetic fuels.

According to one aspect of the present invention, there is provided a method for producing synthetic fuels by hydrogenating carbon monoxide comprising contacting a feed gas containing carbon monoxide and hydrogen with a supported metal sulfide catalyst comprising Pd and at least one promoter selected from the group consisting of alkali metal, alkaline earth metal, and rare earth elements.

According to another aspect of the present invention, there is provided a method for producing synthetic fuels by hydrogenating carbon monoxide comprising contacting a feed gas containing carbon monoxide and hydrogen with a catalyst including a solid acid and a supported metal sulfide comprising Pd and at least one promoter selected from the group consisting of alkali metal, alkaline earth metal, and rare earth elements.

DETAILED DESCRIPTION OF THE INVENTION

The catalyst used in the practice of the invention is a supported metal sulfide comprising Pd and at least one promoter selected from the group consisting of alkali metal, alkaline earth metal, and rare earth elements. The metal sulfide catalyst may be prepared by sulfiding of corresponding Pd compounds.

The sulfiding may be carried out by contacting the Pd compounds with sulfur compounds such as lithium sulfide, sodium sulfide, potassium sulfide, ammonium sulfide, hydrogen sulfide, and thiophene with gradually increasing the temperature up to 150–250° C. and then to a predetermined operation temperature where temperature is maintained for 1–4 hours. The sulfiding may also be carried out by treating the Pd compounds with sulfur compounds contained in high concentrations in a feed gas during the hydrogenation reaction.

The exemplary Pd compounds include metallic palladium such as palladium black, palladium carbon, and palladium on calcium carbonate, palladium complexes or salts such as ammonium tetrachloropalladate $(NH_4)_2PdCl_4$, tetraamminepalladium nitrate $Pd(NH_3)_4(NO_3)_2$, tetraamminepalladium chloride $Pd(NH_3)_4Cl_2$, tetraamminepalladium bromide $Pd(NH_3)_4Br_2$, diamminedichloropalladium $PdCl_2(NH_3)_2$, diamminedinitropalladium $Pd(NH_3)_2(NO_2)_2$, palladium acetate $Pd(CH_3COO)_2$, palladium oxide $PdO$, palladium cyanide $Pd(CN)_2$, palladium chloride $PdCl_2$, palladium bromide $PdBr_2$, palladium iodide $PdI_2$, palladium nitrate $Pd(NO_3)_2$, palladium hydroxide $Pd(OH)_2$, palladium sulfate $PdSO_4$, palladium sulfides $PdS$, $PdS_2$, bis(acetylacetonato) palladium $Pd(C_5H_7O_2)_2$, bis(ethylenediamine)palladium chloride $Pd(C_2H_8N_2)_2Cl_2$, tetrakis(triphenylphosphine) palladium $Pd(PPh_3)_4$, potassium tetracyanopalladium $K_2Pd(CN)_4$, lithium tetrachloropalladate $Li_2PdCl_4$, and calcium tetrachloropalladate $CaPdCl_4$.

The exemplary promoter selected from the group consisting of alkali metal, alkaline earth metal, and rare earth elements include Na, K, Ca, Mg, La, Th, etc. These materials may be used alone or in combination thereof. The promoter may be contained originally in the Pd compounds or supports, or added afterwards. A preferred amount of the promoter is represented by the promoter/Pd molar ratio of 0.01 to 10. The promoter less than 0.01 mol/mol-Pd has little effects on the catalytic activity, while the promoter more than 10 mol/mol-Pd might adversely affect the activity. 0.1 to 1 mol/mol-Pd of the promoter is more preferable. When the promoter is added afterwards, its chlorides, bromides, iodides, oxides, nitrates, phosphates, sulfates, ammonium salts, acetic salts, carbonyls, or chelates may be loaded simultaneously or sequentially with the Pd compound on the support.

The exemplary support materials include inorganic oxides such as silica, alumina, fluorinated alumina, boria, calcia, magnesia, titania, zirconia, silica-alumina, alumina-magnesia, alumina-boria, alumina-zirconia, silica-calcia, silicoalumino phosphate, zeolite, and rare earth metal oxides, clay minerals such as montmorillonite, kaolin, halloysite, bentonite, attapulgite, kaolinite, and nacrite, and carbon. These materials may be used alone or in combination thereof. While any number of materials can serve as a support, magnesia, silica, and calcia are preferred. Metal loading on such supports can improve the activity per unit mass of the loaded metal. The support have a surface area preferably larger than 10 m$^2$/g, and more preferably 100 m$^2$/g. The support having a surface area more than 100 m$^2$/g will provide higher dispersion of metals, eventually leading to higher yields of synthetic fuels. The support may contain nonmetallic elements such as boron and phosphorus.

In preparation of supported catalysts, the support may be impregnated by techniques known as the wet, dry, and vacuum impregnations and the ion exchange method.

The preferred amount of loaded Pd depends on the property of the support and cannot be inclusively determined; preferably it may be 1–30 mass %, more preferably 1–10 mass % of the catalyst. When this amount is less than 1 mass %, the catalyst activity should be lower. On the other hand, when the amount is greater than the above value, the loaded Pd might be agglomerated, so that its activity per unit mass of Pd might be lower.

The sulfide catalyst in the present invention can be used in combination with solid acids. The solid acids include oxides such as alumina, alumina-silica, alumina-boria, alumina-magnesia, and silica-magnesia, zeolites such as X type, Y type, MFI type, and mordenite, and clay minerals such as montmorillonite. γ-alumina is most preferred. These solid acids can be used as supports or mixtures with the sulfide catalyst.

The composite catalyst of the solid acid and the metal sulfide enables the direct synthesis of dimethyl ether (DME) from synthesis gas. DME, a promising next-generation clean diesel fuel, is presently produced with a two-step process: methanol synthesis and following dehydration reaction.

In the present invention, the feed gas containing carbon monoxide and hydrogen is flown over the sulfide catalyst and converted into synthetic fuels such as methanol. When the composite catalyst is used, DME can be produced.

The molar ratio of hydrogen to carbon monoxide ($H_2$/CO) in the feed gas is preferably in the range from 1 to 5, more preferably from 1 to 3. This is because (1) the $H_2$/CO molar ratio in the methanol synthesis reaction ($CO + 2H_2 = CH_3OH$) is 2, and (2) the $H_2$/CO molar ratio in synthesis gases produced from the reforming of natural gas is usually greater than unity, in most cases with excessive hydrogen.

The Pd sulfide catalyst in the present invention may contain metals such as Ti, V, Mn, Fe, Co, Zr, Mo, Ru, and Rh, unless they lessen the effect of the present invention. These materials may be used at the amount from 0.1 to 100 parts by mass of Pd sulfide.

The feed gas may contain sulfur compounds in addition to carbon monoxide and hydrogen. The content of the sulfur compounds is preferably 1–10,000 ppm, more preferably 100–2,500 ppm, most preferably 100–500 ppm.

The product yield is also a function of temperature and pressure. The temperature range is preferably between 100 and 400° C. more preferably between 250 and 350° C. The pressure is preferably between 0.1 and 10 MPa, more preferably between 1 and 7 MPa.

According to the present invention, a feed gas containing carbon monoxide and hydrogen is allowed to react on the specific catalyst, so that we can obtain higher activity and selectivity under lower pressure conditions. Besides this, a simple or no desulfurization unit is required to treat the feed gas because of the excellent sulfur tolerance of the inventive catalyst. This will simplify the manufacturing process of synthetic fuels.

The present invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The present invention is illustrated in more detail by reference to the following examples wherein, unless otherwise indicated, all percentages and ratios are by mass. In the examples, the reaction conditions are as follows:

Reactor system: a high-pressure fixed-bed flow reactor
Synthesis gas composition: 33% CO/62% $H_2$/5% Ar

EXAMPLE 1

Sulfided Ca—Pd/SiO$_2$

A Pd/SiO$_2$ was prepared using the method of A. Gotti and R. Prins in Journal of Catalysis, 175, 302–311(1998): 3.8 ml of 10% tetraamminepalladium nitrate $(Pd(NH_3)_4(NO_3)_2)$ aqueous solution was added dropwise over 3 g of silica having a surface area of 272 m$^2$/g to achieve incipient wetness with the desired loading of 4.5% Pd. The sample was dried at 60° C. for 3.5 hours, 95° C. for 3.5 hours, and then 120° C. for 7 hours, and lastly calcined at 450° C. for 2 hours.

The Pd/SiO$_2$ thus obtained was further impregnated with calcium nitrate $(Ca(NO_3)_2/4H_2O)$ at a Ca/Pd molar ratio of 0.5. The sample was dried at 60° C. for 3.5 hours, 95° C. for 3.5 hours, and then 120° C. for 7 hours.

The resulting Ca—Pd/SiO$_2$ was charged in a stainless reactor and heated at 5° C./min to 400° C. at normal pressure in 5% H$_2$S/H$_2$ flowing at a rate of 12 Nm$^3$/kg-catal./h. The sulfiding was continued until the H$_2$S/Pd molar ratio reached 180. After cooled to ambient temperature, the catalyst was heated again at 5° C./min to 340° C. at 5.1 MPa in the synthesis gas flowing at a rate of 20 Nm$^3$/kg-catal./h.

A methanol yield at steady state was 229 g/kg-catal./h and its selectivity was 90 C-mol %.

EXAMPLE 2

Sulfided La—Pd/SiO$_2$

A sulfided La—Pd/SiO$_2$ was prepared in the same manner as Example 1 except that calcium nitrate was replaced by lanthanum nitrate $(La(NO_3)_3.6H_2O)$ at a La/Pd molar ratio of 0.5.

At the same reaction conditions as Example 1, a methanol yield at steady state was 210 g/kg-catal./h and its selectivity was 64 C-mol %.

EXAMPLE 3

Sulfided Ca—Pd/SiO$_2$ 1 ml of 10% tetraamminepalladium nitrate $(Pd(NH_3)_4(NO_3)_2)$ aqueous solution was added dropwise over 4 g of silica having a surface area of 560 m$^2$/g. The sample was dried at 60° C. for 3.5 hours, 95° C. for 3.5 hours, and 120° C. for 7 hours. These procedures of impregnation and drying were repeated another 4 times to achieve incipient wetness with the desired loading of 4.5% Pd. Then the sample was calcined at 450° C. for 2 hours.

The resulting Pd/SiO$_2$ was further impregnated with calcium nitrate $(Ca(NO_3)_2.4H_2O)$ at a Ca/Pd molar ratio of 0.1. Then the sample was dried at 60° C. for 3.5 hours, 95° C. for 3.5 hours, and 120° C. for 7 hours. Lastly the sample was sulfided in the same manner as Example 1.

At the same reaction conditions as Example 1, a methanol yield at steady state was 420 g/kg-catal./h and its selectivity was 85 C-mol %.

EXAMPLE 4

Sulfided Ca—Pd/SiO$_2$

A sulfided Ca—Pd/SiO$_2$ was prepared and subjected to the reaction in the same manner as Example 3 except that the Ca/Pd molar ratio was changed from 0.1 to 0.5, and that the reaction temperature from 340° C. to 320° C., and that the flowing rate of synthesis gas from 20 Nm$^3$/kg-catal./h to 30 Nm$^3$/kg-catal./h.

A methanol yield at steady state was 730 g/kg-catal./h and its selectivity was 93 C-mol %.

Comparison 1 Pd/SiO$_2$

A Pd/SiO$_2$ prepared in the same manner as Example 1 was charged in a stainless reactor and heated at 5° C./min to 450° C. in H$_2$ flowing at a rate of 18 Nm$^3$/kg-catal./h for 3 hours. A pressure on stream was 0.3 MPa. After cooled to ambient temperature, the catalyst was heated again at 2.5° C./min to 340° C. in the synthesis gas flowing at a rate of 19 Nm$^3$/kg-catal./h. A pressure on stream was 5.1 MPa.

A methanol yield at steady state was 220 g/kg-catal./h and its selectivity was 86 C-mol %.

Similarly the Pd/SiO$_2$ was charged in a stainless reactor and heated at 5° C./min to 400° C. at normal pressure in 5% H$_2$S/H$_2$ flowing at a rate of 12 Nm$^3$/kg-catal./h. The sulfiding was continued until the H$_2$S/Pd molar ratio reached 180. After cooled to ambient temperature, the catalyst was heated again at 5° C./min to 340° C. in the synthesis gas flowing at a rate of 20 Nm$^3$/kg-catal./h. A pressure on stream was 5.1 MPa. A methanol yield at steady state was 60 g/kg-catal./h and its selectivity was 73 C-mol %.

Comparison 1 shows that sulfiding of the Pd/SiO$_2$ reduced the methanol yield to a quarter. On the other hand, the inventive catalysts (Examples 1–4) show 1–3 times higher activity than the Pd/SiO$_2$ and 4–12 times higher than the sulfided Pd/SiO$_2$.

EXAMPLE 5

A mixture of the synthesis gas and H$_2$S was flowed over a sulfided Ca—Pd/SiO$_2$ prepared in the same manner as Example 4, after the steady state in the synthesis gas was achieved. The concentration of H$_2$S was 100 ppm.

Table 1 shows methanol yields before and during the introduction of H$_2$S. The yields during the H$_2$S feed were determined when the H$_2$S/Pd molar ratio reached 0.2 and 6.0.

Comparison 2 Commercial Catalyst

A commercial catalyst (60% CuO/30% ZnO/10% Al$_2$O$_3$, 32–42 mesh) was heated in the synthesis gas flowing at a rate of 6 Nm$^3$/kg-catal./h at 5.1 MPa using the following sequence: at 4° C./min to 120° C., where the temperature was maintained for 90 min, then at 1° C./min to 210° C., maintained for 12 hours, and finally at 1° C./min to 240° C.

Table 1 shows methanol yields before and during the introduction of H$_2$S. The yields during the H$_2$S feed were determined when the H$_2$S/Cu molar ratio reached 0.2 and 0.3.

TABLE 1

|  | Methanol Yields/g/kg-catal./h | |
|---|---|---|
|  | Example 5 | Comparison 2 |
| Before H$_2$S feed | 530 | 120 |
| During H$_2$S feed | | |
| H$_2$S/(Pd,Cu) = 0.2 | 290 | 75 |
| H$_2$S/Cu = 0.3 |  | 60 |
| H$_2$S/Pd = 6.0 | 220 |  |

Table 1 shows that the inventive catalyst in Example 5 yields larger amount of methanol than the commercial catalyst in Comparison 2 during the H$_2$S feed as well as prior to the H$_2$S feed. Besides that, the inventive catalyst has an almost constant activity during the H$_2$S feed.

Additional advantages and modifications will readily occur to those skilled in the art. Therefore, the invention is its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing methanol and/or dimethylether by hydrogenating carbon monoxide comprising contacting a feed gas containing carbon monoxide and hydrogen with a magnesia, silica or calcia supported metal sulfide catalyst comprising Pd and at least one promoter selected from the group consisting of alkali metal, alkaline earth metal, and rare earth elements.

2. The method according to claim 1, wherein said catalyst is supported on magnesia.

3. The method according to claim 1, wherein said catalyst is supported on silica.

4. The method according to claim 1, wherein said catalyst is supported on calcia.

5. The method according to claim 1, wherein said feed gas contains from 1 to 10000 ppm of sulfur compounds.

6. The method according to claim 1, wherein said feed gas contains from 100 to 2500 ppm of sulfur compounds.

7. The method according to claim 1, wherein said feed gas contains from 100 to 500 ppm of sulfur compounds.

8. The method according to claim 1, wherein a molar ration of hydrogen to carbon monoxide is from 1:1 to 5:1 and said feed gas is contacted with said catalyst at a temperature of 100 to 400° C. and at a pressure of 0.1 to 10 MPa.

9. The method according to claim 1, wherein a molar ratio of hydrogen to carbon monoxide is from 1:1 to 3:1 and said feed gas is contacted with said catalyst at a temperature of 250 to 350° C. and at a pressure of 1 to 7 MPa.

10. The method according to claim 5, wherein a molar ratio of hydrogen to carbon monoxide is from 1:1 to 5:1 and said feed gas is contacted with said catalyst at a temperature of 100 to 400° C. and at a pressure of 0.1 to 10 MPa.

11. A method of producing methanol and/or dimethylether by hydrogenating carbon monoxide comprising contacting a feed gas containing carbon monoxide and hydrogen with a catalyst including a solid acid and a magnesia, silica or calcia supported metal sulfide comprising Pd and at least one promoter selected from the group consisting of alkali metal, alkaline earth metal, and rare earth elements.

12. The method according to claim 11, wherein said solid acid is γ-alumina.

13. The method according to claim 12, wherein said catalyst is supported on magnesia.

14. The method according to claim 12, wherein said catalyst is supported on silica.

15. The method according to claim 12, wherein said catalyst is supported on calcia.

16. The method according to claim 11, wherein said feed gas contains from 1 to 10000 ppm of sulfur compounds.

17. The method according to claim 11, wherein said feed gas contains from 100 to 2500 ppm of sulfur compounds.

18. The method according to claim 11, wherein said feed gas contains from 100 to 500 ppm of sulfur compounds.

19. The method according to claim 11, wherein a molar ratio of hydrogen to carbon monoxide is from 1:1 to 5:1 and said feed gas is contacted with said catalyst at a temperature of 100 to 400° C. and at a pressure of 0.1 to 10 MPa.

20. The method according to claim 11, wherein a molar ratio of hydrogen to carbon monoxide is from 1:1 to 3:1 and said feed gas is contacted with said catalyst at a temperature of 250 to 350° C. and at a pressure of 1 to 7 MPa.

21. The method according to claim 16, wherein a molar ratio of hydrogen to carbon monoxide is from 1:1 to 5:1 and said feed gas is contacted with said catalyst at a temperature of 100 to 400° C. and at a pressure of 0.1 to 10 MPa.

22. The method according to claim 1, wherein the amount of Pd in said catalyst is 1–10 mass % of said catalyst.

* * * * *